United States Patent [19]
Johnson

[11] 4,166,102
[45] Aug. 28, 1979

[54] IMMOBILIZED IMMUNOADSORBENT

[75] Inventor: Lavell R. Johnson, Salt Lake City, Utah

[73] Assignee: Becton, Dickinson and Company, East Rutherford, N.J.

[21] Appl. No.: 802,075

[22] Filed: May 31, 1977

Related U.S. Application Data

[62] Division of Ser. No. 565,848, Apr. 7, 1975, Pat. No. 4,059,685.

[51] Int. Cl.² ............................................. G01N 33/16
[52] U.S. Cl. ...................................... 424/1; 23/230 B; 424/12
[58] Field of Search .............................. 424/1, 12, 1.5; 23/230 B

[56] References Cited
U.S. PATENT DOCUMENTS

| 3,505,785 | 4/1970 | Kirkland | 55/67 |
| 3,639,558 | 2/1972 | Csizmas | 424/12 |
| 3,853,987 | 12/1974 | Dreyer | 424/1 |
| 3,896,217 | 7/1975 | Johnson | 424/1 |

Primary Examiner—Benjamin R. Padgett
Assistant Examiner—Christine M. Nucker
Attorney, Agent, or Firm—Smyth, Pavitt, Siegemund, Jones & Martella

[57] ABSTRACT

An immobilized immunoadsorbent for use in immunoassay and radioimmunoassay procedures includes, in a preferred form, a mass of superficially porous refractory particles having a water insoluble polymer, such as dextran, bonded thereto. The polymer in turn has bonded to it, by covalent bonds, antibodies capable of binding a specific antigen thereto and stoichiometrically releasing the bound antigen by the use of a rinsing solution which does not adversely affect the binding of the antibody to the polymer. Preferably, each of the porous particles includes an impervious core which has joined thereto sufficient layers of microparticles to form an outer porous coating on the core. Methods of forming such an immunoadsorbent and for using the same and structure for supporting the same are also disclosed.

5 Claims, 2 Drawing Figures

IMMOBILIZED IMMUNOADSORBENT

This is a division of application Ser. No. 565,848, filed Apr. 7, 1975, now U.S. Pat. No. 4,059,685.

RELATED APPLICATIONS

Reference is made to application Ser. No. 342,513, filed Mar. 19, 1973, assigned to the same assignee.

BACKGROUND OF THE INVENTION

This invention relates to immunoadsorbents and more particularly to an improved immunoadsorbent for use in immunoassay procedures such as radioimmunoassay wherein the immunoadsorbent may be used for repeated assays.

STATE OF THE ART

Radioimmunoassay is an analytical technique which depends upon the competition (affinity) of antigen for antigen-binding sites on antibody molecules. In practice, standard curves are constructed from data gathered from a plurality of samples each containing (a) the same known concentration of labelled antigen, and (b) various, but known, concentrations of unlabelled antigen. Antigens are labelled with a radioactive isotope tracer. The mixture is incubated in contact with an antibody, the free antigen is separated from the antibody and the antigen bound thereto, and then, by use of a suitable detector, such as a gamma or beta radiation detector, the percent of either the bound or free labelled antigen or both is determined. This procedure is repeated for a number of samples containing various known concentrations of unlabelled antigens and the results plotted. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In actual analysis, the sample in which the concentration of antigen is to be determined is mixed with a known amount of tracer antigen. Tracer antigen is the same antigen known to be in the sample but which has been labelled with a suitable radioactive isotope. The sample with tracer is then incubated in contact with the antibody. Thereafter, it may be counted in a suitable detector which counts the free antigen remaining in the sample. The antigen bound to the antibody or immunoadsorbent may also be similarly counted. Then, from the standard curve, the concentration of antigen in the original sample is determined. Afterwards, the antibody or immunoadsorbent mass is discarded.

In order to detect the percentage of antigen that is bound to the antibody (bound antigen) and/or the percentage that remains free or unbound it is necessary to first separate the sample into a fraction containing bound antigen and one containing only free antigen. One common method for doing this is to add a dextran coated charcoal to the mixture. The dextran permits the unbound antigen, of lower molecular weight than the bound antigen, to pass through the dextran and the charcoal adsorbs the free antigen. The charcoal with adsorbed free antigen is then separated from the antibody (and bound antigen) by centrifugation.

Another known procedure is to add to the mixture another antibody which selectively precipitates the first antibody (with the bound antigen) thus leaving in solution only free antigen. Classification into appropriate free and bound fractions is then effected by separating the precipitate from the supernatant by centrifugation or other suitable means. Some workers have resorted to the technique of binding the antibody to the inner walls of a plastic vessel, filling the vessel with the antigen bearing sample, allowing it to stand for an incubation period that typically ranges from 4 to 72 hours and then separating free antigen from bound antigen by draining and rinsing the vessel leaving therein only the antibody and bound antigen. A more recently developed technique is to prepare the immunoadsorbent by binding the antibodies onto an insoluble cross-linked dextran. The immunoadsorbent and antigen bearing sample are incubated then the dextran with bound antigen is separated from the solution by suitable means.

In all of the foregoing procedures, the percentage of labelled antigen in either or both the bound or free fractions is determined and the standard curve used to determine the antigen concentration. Thereafter, the immunoadsorbent is discarded.

Although the foregoing radioimmunoassay techniques have proven to be valuable tools and have gained widespread acceptance, they are still not all that are to be desired because the antibody (immunoadsorbent) is consumed with each analysis hence must be discarded. Moreover, prior practice is batch type and the several reagents are added to the antibody in test tubes in which the separate steps, such as incubation, rinsing and the like, are performed, thus resulting in a slow and costly operation.

The above-identified application describes a substantial improvement in immunoassay procedures in that the same immunoadsorbent may be used repeatedly for many assays by releasing from the immunoadsorbent the antigen which is bound to the antibody mass, the latter immobilized on the substrate; i.e. selectively and stoichiometrically releasing all of the antigen on the immunoadsorbent after the assay is completed. It is to a reusable immunoadsorbent that the present invention is directed.

DESCRIPTION OF THE PRIOR ART

It is known from the literature that antibodies may be isolated by use of immunologic adsorbents, the technique being useful for isolation and purification of antibodies rather than quantitative determination thereof, see Campbell et al, *Proc. Nat'l. Acad. Sci. U.S.* 37 (1951) 575.

The use of an antibody coupled to an insoluble polymer for extracting specific antigens for purposes of isolating and purifying the same is described in Weetall et al, *Biochem. Biophys. Acta.* 107 (1965) 150-152.

Porous glass has been described as a substrate for immobilizing enzymes, see Weetall, *Biochem. Biophys. Acta.* 212 (1970) 1-7. There, glass was treated with gammaaminopropyltriethoxysilane and the isothiocyanate derivative was prepared by treatment with thiophosgene. The enzyme was coupled to the isothiocyanate derivative. Also described in the preparation of an arylamine derivative by the reaction of alkylamine glass with P-nitrobenzoyl chloride followed by use of sodium dithionate to reduce the nitro groups. The arylamine glass was then diazotized and the enzyme coupled thereto.

Weetall, in *Biochem. J.* (1970) 117, 257-261 also describes the use of antibodies bound to porous glass through a silane coupling agent, the immunoadsorbent being used to isolate and purify specific antigens. The data given, however, shows that the reused column, in which the antigen was eluted from the immobilized antibody immunoadsorbent was quite erratic in performance since the recovery of released antigen varied from 74% to 100%. See also U.S. Pat. No. 3,652,761 of Mar. 28, 1972. While useful as an isolation system, the described system has considerable objections from the standpoint of a useable tool in quantitative analysis in which there must be substantially stoichiometric release of the antigen.

U.S. Pat. No. 3,555,143 of Jan. 12, 1971, relates to radioimmunoassay procedures in which an immobilized immunoadsorbent is used only once and then discarded. The immunoadsorbent is a dextran (Sephadix G 25, superfine) cross-linked with glycerine ether bridges and substituted with p-nitrophenoxy-hydroxy-propyl ether groups. The nitro groups are reduced to amine groups using sodium dithionite. The Sephadex substituted with p-amino-phenoxy-hydroxy-propyl groups was then treated with thiophosgene to form Sephadex substituted with p-isothiocyanate-phenoxy-hydroxypropyl groups, the antibody being bound to the latter substituted product.

A reaction widely used to insolubilize a protein involves a covalent binding of the protein to a cyanogen bromide activated cellulose matrix. The mechanism of such activation is set forth in Bartling et al, *Biotechnology and Bioengineering*, Vol XIV (1972) 1039–1044.

U.S. Pat. Nos. 3,502,888 of July 13, 1971; 3,639,559 of Feb. 1, 1972, and 3,720,760 of Mar. 13, 1972 are also of interest.

Where an immobilized immunoadsorbent is to be used only once and discarded, the long term properties of the substrate are not of major consequence. Thus, materials such as Sephadex (dextran) or Sepharose (beaded agarose product) operate satisfactorily as substrates for antibodies bound thereto as described in U.S. Pat. No. 3,555,143, supra. Where the immunoadsorbent is to be used repeatedly, as described in the above-identified application Ser. No. 342,513, certain problems arise.

One of the objections is the tendency of Sephadex and Sepharose type products to dehydrate, that is, the gel collapses and packs to such an extent that flow through the mass is substantially impeded and the availability of antibody for binding antigen is altered, thus affecting the reproducibility and stability of the immunoadsorbent for repeated use.

Glass and other solid inorganic materials offer a desirable alternative because they can be formed into beads to provide better flow and easier packing into a column type arrangement. Such materials do not collapse and are not subject to dehydration during periods of extended use. While a desirable alternate, glass type products also suffer from disadvantages. One of the problems is obtaining a sufficient binding of the antibody to the substrate. Either an insufficient initial binding takes place to provide the activity needed for a quantitative analysis tool, or the activity changes over the life of the immunoadsorbent by undesirable release of antibodies.

Where the glass is highly porous, as that used by the Weetall references cited, there is so much active glass surface area that ample binding of the antibody takes place but non-specific binding of the antigen also takes place. Thus, the antigen bound to the glass is not released completely. That is, rather than having a stoichiometric release, for each use thereof, as is needed for quantitative analysis, the release characteristics are variable and unpredictable. This is confirmed by the Weetall data. Since such glass is usually 96% air or void space, there is considerable active surface area of the glass, not occupied by antibody which serves as an antigen binding site.

Another difficulty with highly porous glass products is that there are multiple crevices in the pores which result in trapping in the crevices and slow release because of the slow diffusion in the crevices. Where a fast response is needed, as for example in automated equipment, the diffusion of the reactants is a rate limiting step and, as is well known, diffusion may be a relatively slow process. Thus, even if not bound to the substrate, the diffusion of the antigen is relatively slow and thus, for the purpose of rapid automated assay equipment, the antigen is effectively bound rather than being rapidly and stoichiometrically released.

Superficially porous supports are known for use in chromatography, see for example U.S. Pat. No. 3,505,785 of Apr. 14, 1970 which describes a product commercially available from E. I. du Pont de Nemours and Co. under the trademark "Zipax". These support beads for use as chromatographic column packing consists of a plurality of discrete macroparticles with impervious cores and having irreversibly joined thereto a coating of a series of sequentially adsorbed-like monolayers of like colloidal microparticles. Thus, spherical glass microbeads of about 30 microns diameter include an outer porous surface crust which is about one micron thick. Such a material, if used as a substrate offers substantial surface area for the desired activity but the substrate must be properly prepared to assure the proper quick response as well as stoichiometric release.

Thus, the provision of a reusable immunoadsorbent and which stoichiometrically releases the antigen for each assay is quite desirable. Where that immunoadsorbent is also substantially free of dehydration and packs such that the flow quality through the mass is of desirable character over the useful life of the immunoadsorbent, a substantially improved reuseable immobilized immunoadsorbent is provided.

SUMMARY OF THE INVENTION

In accordance with this invention, an improved immobilized immunoadsorbent is provided for use and reuse in radioimmunoassay procedures. The substrate or basic matrix is stable against dehydration and collapse and is in the form of a mass of solid particles each having an outer surface of high surface area. A typical such substrate is composed of superficially porous refractory particles, each of which includes an impervious core having joined thereto sufficient layers of microparticles to form an outer porous coating on the core to provide a high surface area.

To the substrate is bonded a water insoluble polymer material. The polymer may be bonded by treating the substrate to form an amino alkylsilane derivative thereof followed by treatment to form an isothioayanoalkylsilane derivative to which the polymer is bound. Typical of the useful polymer materials is dextran.

The dextran operates as a barrier to cover the active sites on the substrate to which antigen may be bound in sich a way as to interfere with subsequent assays. Since the immunoadsorbent of this invention is used and reused, by use of an eluting medium which separates the antigen from the bound antibodies, the release of any antigen which may be bound to the substrate creates errors in subsequent assays. The error arises because of the unpredictable and unknown amount retained or released. Thus, the polymer affectively operates as a barrier to prevent the substrate from binding antigen.

The polymer is then activated to bind antibody through a covalent bond by treatment with cyanogen bromide, the mechanism of the reaction being as described in Bartling et al, supra.

The resultant immobilized immunoadsorbant is then placed in a chamber holder of a unique structure for use on automated equipment as described in the above application Ser. No. 342,513.

DETAILED DESCRIPTION OF THE INVENTION

Figure 1:
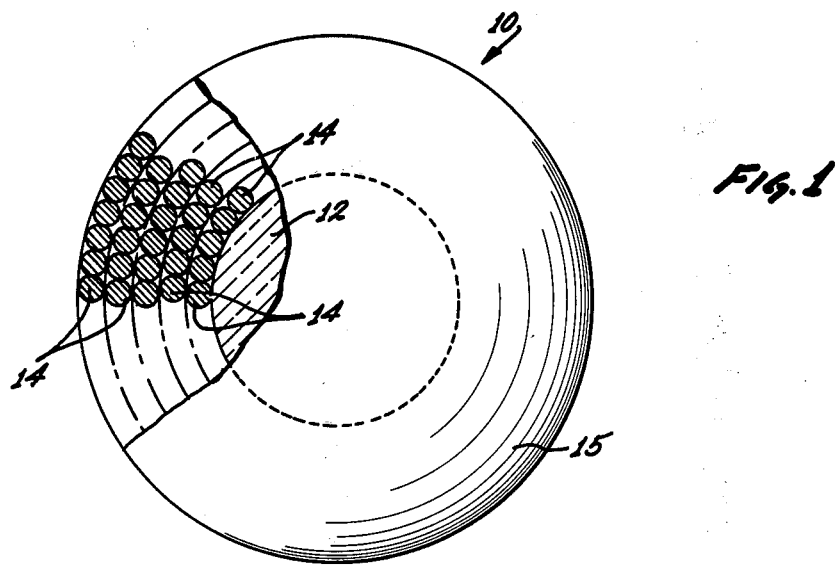
FIG. 1 is a view in perspective with a portion thereof broken away and in section to illustrate diagrammatically the substrate useable in accordance with this invention.

The improved immobilized immunoadsorbent of the present invention is intended for use principally in radioimmunoassay procedures.

Typical of the materials which may be quantitatively determined by the system of the present invention are the following: estriol, digoxin, digitoxin, testosterone, estradiol, aldosterone, progesterone, cortisol, 11-desoxycortiosterone, 11-desoxycortisol, thyroid hormones such as thyroxin ($T_4$) triiodothyronine ($T_3$), polypeptides such as angiotensin, TSH (thyroid stimulating hormone), ACTH, GH (growth hormone), HP (human placento-lactogen), parathormone, calcitonin, insulin, glucagen, polypeptide proteins such as CEA (carcino embrionic antigen), alphafetoprotein, interferon, viruses such as Australia antigen, vitamins such as D and $B_{12}$ folic acid and drugs such as dilantin and barbiturates, to mention only a few.

The antisera for the above antigens are known, as are the labelled antigens, available in the form of radioactive isotope labelled materials, usually in the form of the $I^{125}$ isotope or $H^3$ isotope.

The immobilized immunoadsorbent of this invention includes a substrate with which the antibodies are relatively permanently associated. In use, an unlabelled antigen sample with a known concentration of labelled antigen is brought into contact with the immobilized immunoadsorbent disposed in a chamber holder. When brought into contact, a portion of the mixture of labelled antigen and unlabelled antigen binds to the specific antibody bound on the substrate. Thereafter, the unbound antigen or the bound antigen or both are counted and concentration of the unlabelled antigen is determined from standard data.

Thereafter, the immobilized immunoadsorbent is rinsed with an appropriate aqueous solution containing solvents such as methyl alcohol, isopropy alcohol or ethyl alcohol as well as dimethyl formamide to effect a stoichiometric release of the bound labelled and unlabelled antigen from the immobilized immunoadsorbent. The rinsing or eluting operation effectively regenerates the immunoadsorbent for reuse, and thereafter, the same immunoadsorbent may be used again, repeatedly, for assays of that antigen as to which the immobilized antibody is specific, with washings, as described between each use.

Since the antigen material is flowed into a chamber supporting the immunoadsorbent which is reused, the flow characteristic of the substrate should be such that contact is achieved between the supported antibodies and antigen mixture. Moreover, the substrate must be of such a type as not to interfere with release of the bound antigen while retaining the bound antibody. Reproducibility, stability and speed are some of the advantages of the improved method, and thus the substrate must be such that sufficient activity may be obtained in terms of bound antibody with available antigen binding sites. It is preferred, therefore, that the substrate be particulate, and spherical i.e. formed of a mass of discrete particles since this enhances the desirable flow-through character of not only the sample mixture of labelled and unlabelled antigen, but of the rinse or eluting medium as well.

Particulate materials capable of providing the needed antibody actively unknown, e.g. Sephadex, Sepharose, porous glass and the like. Materials such as Sephadex and Sepharose are gel type materials and over periods of extended use, tend to dehydrate resulting in collapse with resulting packing which impedes the flow. Materials such as porous glass are so active that antigen is bound to the glass and not released.

Thus, an important aspect of this invention is the formation of a barrier coating over a particulate substrate, the barrier coating operating to provide, in effect, a mask which precludes the potentially active sites on the substrate from irreversibly binding the antigens. The barrier also functions as an immobilized component of the substrate to which the antibodies may be attached. Since assays are conducted in aqueous and non-aqueous solvents, the barrier coating is preferably insoluble and not adversely affected by the solvents and solutions used in the procedure. Water insoluble polymer materials such as dextran are preferred in accordance with this invention.

The substrate itself is preferable a particulate material resistant to dehydration and collapse. Rapid mass transfer at relatively high flow rates are a function of substrate geometry, and packing character in the chamber holder. A preferred substrate is a material having a controlled surface porosity, superficially porous refractory particles made up of discrete macroparticles with impervious non-porous cores, and having joined ther to a coating of a series of sequentially adsorbed like monolayers of like inorganic microparticles.

Referring to FIG. 1, for purposes of illustration, the superficially porous refractory particle 10 which forms the substrate for the immobilized immunoadsorbent includes a core 12 in the form of a macroparticle which is an impervious non-porous core. The core 12 is shown as spherical because this shape is preferred for packing purposes. The core, in the form of a sphere is of a diameter of between 5 and 500 microns in diameter and composed of glass, although it may be of sands, ceramics, and the like.

The cores are preferably of uniform size i.e. all within about 50% of the average diameter. Affixed to the core 12 is a plurality of layers of microparticles 14 which form an outer porous coating. The microparticles may range in size from 5 milimicrons to 1 micron, and the number of layers may be between 2 and 30. The microparticles may be amorphous silica, alumina, thoria and the like.

As will be apparent, a substrate of material as described has a relatively high surface area due to the porous coating 15, but is relatively free of pores in the core material. For beads of an overall diameter of 30 microns, and a porous crust of one micron, a surface area of between 0.8 to 1.0 m$^2$/gram is obtained, with a packed bed density of 1.5 g/cc. The regular geometry, the stability against dehydration and collapse, and the bulk renders the above material quite exceptional as a substrate.

However, there is a tendency for such a material, if used in the form described as a substrate directly for the antibody material, to contain active sites which tend to bind the antigen mixture of a component thereof in a non-releasable manner. This problem may be quite objectionable where the immobilized immunoadsorbent is reused, an important objective in this invention. Since the accuracy and speed of the assay is, in part, related to the ability of the antibody to bind the antigen and stoichiometrically release the same when rinsed, any unreleased antigen adversely affects the accuracy of subsequent assay. While a background count could be taken, this is not entirely satisfactory since the retention-release phenomena tends to be non-uniform and non-predictable.

By this invention, such a tendency is eliminated by the use of a barrier coating adhered to the substrate through a silane coupling agent, i.e. the polymer is bound directly to the outer surface portions of the substrate by silane linkages. The polymer is then activated by treatment with cyanogen bromide which covalently binds the protein (antibody) to the polymer activated particulate substrate. The polymer coating not only acts as a barrier, effectively to mask latent active sites on the substrate proper, but offers an active surface to which the antibody may be covalently bound, a bond recognized as relatively strong.

In a typical procedure, in accordance with this invention, 12 grams of particulate substrate material (30 micron diameter superficially porous rafractory particles, as described supra) were added to a 500 ml flask to which was added 20 ml (18.84 grams) of 3-aminopropyltriethoxysilane and 180 ml of toluene. The mixture was refluxed for 22 hours to form the aminoalkylsilane derivative of the glass substrate. The derivative was filtered, washed with 200 ml of toluene while on the filter support, and air dried, followed by a second washing with 100 ml of chloroform and a second air drying.

The isothiocyanoalkylsilane derivative was prepared by treating the prepared aminoalkylsilane glass derivative with 16.6 ml (25 grams) of thiophosgene and 150 ml of chloroform. The reaction vessel was protected from light and refluxed for 18 hours to form the described derivative, which was filtered, washed in chloroform, and air dried.

The result of the steps thus far was to prepare an "activated" substrate to which the water insoluble polymer may be bound.

In accordance with this invention it is preferred to use dextran of a molecular weight of 70,000, although other materials may be used.

Accordingly, two hundred ml of a 1% solution of dextran in 0.1 m sodium bicarbonate, pH 9.0, were added to the "activated" substrate. The mixture was stirred for three hours, filtered, washed with 300 ml of water, washed with 100 ml of acetone and air dried to provide 11.6 grams of polymer coated particulate substrate.

The remaining steps in the procedure involve activation of the polymer coated substrate and, optionally, the purification of the antibody, and binding the antibody to the coated substrate, sometimes referred to as the conjugation of the antibody to prepared substrate.

To activate the dextran, twenty grams of cyanogen bromide were dissolved in 200 ml of water. Cyanogen bromide is quite toxic and therefore standard safety precautions are taken. The dextran coated substrate was added (11.6 grams) and the mixture stirred. The pH was raised from 3.6 to pH 10-11 using 23 ml of 6 N sodium hydroxide. The pH was maintained between 10 and 11 by the addition of 6 N sodium hydroxide for two minutes. The activated dextran coated substrate was then washed with 400 ml of water, 400 ml of 50%, on a volume basis, of water and acetone, 400 ml of 25%, on a volume basis, of water and acetone and finally 400 ml of acetone. The product was then air dried.

Treatment of the polymer coated substrate with cyanogen bromide results in reaction with adjacent hydroxyl groups on the polymer to form an imidocarbonate which couples with the nucleophilic groups (amino) on the antibody to form the carbonic acid ester on hydrolysis. Rapid hydrolysis of the imidocarbonate in acid media results in formation of a cyclic carbonate which is not as efficient in binding as the imidocarbonate. Thus, care should be taken to avoid conditions promoting cyclic carbonate formation.

Simple purification of the antibody prior to conjugation may optionally be conducted as follows: one ml of 18% sodium sulfate was added to 0.1 ml of the antisera. The solution was vortexed and incubated for one hour to precipitate gamma globulins. The resulting mixture was then centrifuged for five minutes at 1000 xg at room temperature followed by decanting and discarding the supernatant. The pellet was suspended in 10 ml of 18% sodium sulfate with addition of 0.10 ml of water. The resulting mixture was then vortexed and centrifuged again. The supernatant is decanted while the pellet was dissolved in 0.8 ml of 0.1 M sodium bicarbonate solution.

It is preferred in accordance with the present invention to conjugate the antibody to the substrate while the latter is saturated with antigen as to which it is specific. The reason for this procedure is to obtain enhanced activity by protecting the active sites on the antibody during the conjugation procedure, thus, in effect assuring that the antibody will assume a relation with the substrate which assures availability of active sites. In a sense, the binding of the active sites with antigen allows an orientation of the antibody which reduces masking of the sites by the conjugation procedure.

Thus, a 0.5 ml aliquot of a 0.1 mg/ml solution of antigen, specific to the antibody, was dissolved in an ethanol-water solution (2 parts ethanol and 1 part water) and dried down in a test tube with nitrogen gas. The purified antisera, dissolved in 0.8 ml of 0.1 M sodium bicarbonate, or 0.1 ml of antisera in 0.8 ml of 0.1 M sodium bicarbonate was added to the tube containing the dried antigen followed by incubation for one hour in a capped culture tube. Thereafter, 300 mg of the cyanogen activated polymer coated substrate were added to the tube containing the antibody solution and incubated for one to three days at 4° C. while mixing. During the incubation period the conjugation takes place with the antibody having its antigen binding sites protected by bound antigen.

After incubation, the suspension was centrifuged at 1000 xg for five minutes and the supernatant decanted and discarded. The pellet was washed two times with 10 ml of 0.5 M sodium bicarbonate solution. After each wash the suspension was centrifuged and the supernatant discarded. The antibody coated substrate was then washed two times with 10 ml of 0.1 M acetate buffer, pH 4. The antibody coated substrate was then washed with 10 ml of 0.05 M phosphate buffer, pH 7.5, containing 0.5 sodium chloride and 0.5% bovine serum albumin and 0.02% sodium azide as a preservative. The resulting product was then resuspended in 10 ml of the last wash solution and stored at 4° C.

The resultant product, prior to use in an assay, is rinsed with one of the solutions described to release the antigen bound to the immobilized antibody. In storage, however, it is preferred that the antigen remain bound to the antibody.

It is possible, in accordance with this invention to conjugate the antibody, in a free state, to the substrate. This procedure involves admixing the antibody to the cyanogen activated polymer coated substrate followed by incubation and post treatment as already described.

Figure 2:
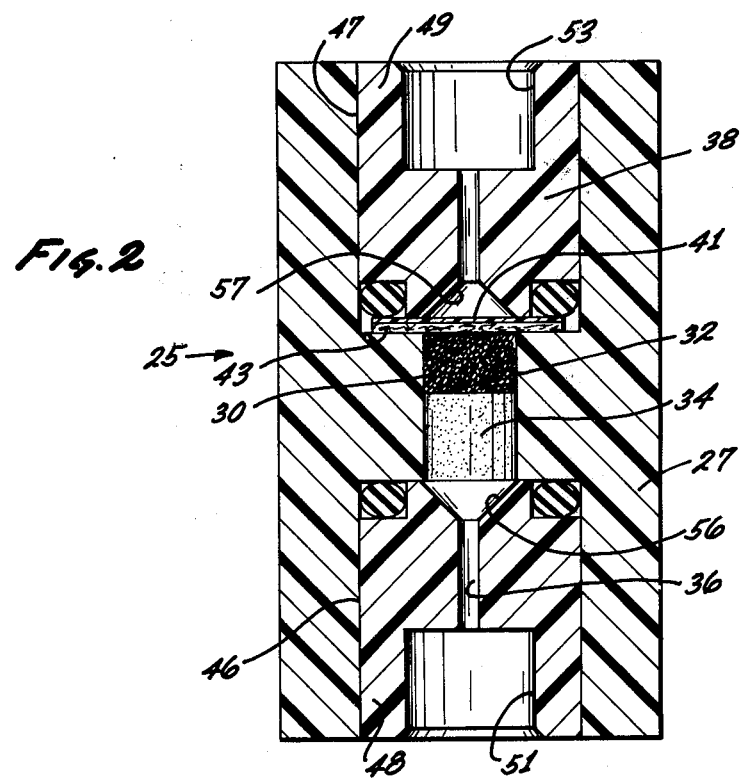
FIG. 2 is a view in section of a chamber holder in accordance with this invention.

One aspect of the present invention involves the provision of a chamber holder for the immobilized immunoadsorbent. Referring to FIG. 2, the chamber holder 25 includes a supporting body 27 which is cylindrical in shape for ease of installation. Provided within the body 27 is a chamber 30 which contains the immobilized immunoadsorbent matter 32, illustrated as particulate material. The immunoadsorbent is supported in the chamber by a porous plug 34 whose pore size is smaller than the particles making up the immunoadsorbent. An outlet 36 is provided for exit of material flowed through the chamber through an inlet 38. The plug 34 is press fitted in the support body which may be of a plastic material such as polypropylene or "DERLIN". By way of example, the chamber is ⅛ inch in diameter and ¼ inch long while the plug is ⅛ inch by ⅛ inch 10 micron pore size.

Positioned in the inlet path are filter elements 41 and 43, the form 400 mesh nylon screen which bears against a filter disc 43 preferably of polytetrafluoroethylene and in the form of a felt, 10 micron or less in pore size.

As illustrated, the chamber 30, at each end thereof terminates in enlarged end sections 46 and 47, in the form of counter-bores each of which receives a press fitted plug 48 and 49, respectively. Each plug includes an interior counter-bore, 51, 53, respectively, and a passage therethrough, as illustrated. On the ends of the plugs facing the chamber 30, the plugs include a diverging conical opening 56, 57, and an annular shoulder which receives an o-ring seal element, as shown, the latter forming a seal in the respective counter-bored ends of the support body 27.

Plug 49 operates to compress filters 41 and 43 in place, the screen 41 operating to prevent the felt from entering the conical opening 57.

Attachment to the chamber holder is through the end plugs 48, 49 and the end bores 51, 53 thereof. Thus, the chamber holder is removed as a unit and replaced with a chamber holder for an immunoadsorbent of an antibody specific to the antigen being run in that particular assay. When not used, the appropriately identified chamber holder may be stored at 4° C.

Chamber holders as described for supporting immobilized immunoadsorbents have been used in assays of the various antigens identified. The immunoadsorbents of this invention have been used for over 500 assays for each immunoadsorbent and still continue to function with results favorable to those obtained with the classical methods, i.e. standard deviation of between 5% and 6%.

The chamber holder includes a diverging cone 57 in the inlet end to the chamber for the purpose of dispersing the flow over the bed of the particulate immunoadsorbent in the chamber 30. Diverging opening 56 operates as a collector for the material exiting, while plug 46 supports the porous plug 34 within the chamber.

While dextran has been described as a useable polymer, the invention is not limited to that specific material. Other water insoluble polymer materials with available hydroxy groups for cyanogen bromide activation may be used, e.g. cellulose and the like. Dextran is preferred, however, because of the considerable use of this material in radioimmunoassay in the prior art, e.g. dextran coated charcoal, and its behavior in the environment is not detrimental to the procedure.

It will be apparent to those skilled in the art that various modifications may be made with respect to the subject matter herein disclosed. For example, the barrier coating may be used to mask other substrates where activity of the substrate is a potential problem. Other modifications, changes and alterations will be apparent from the foregoing description of illustrative forms of the invention without departing from the scope of the invention as set forth in the appended claims.

I claim:

1. In a radioimmunoassay procedure wherein a known amount of a labelled antigen and an unknown and unlabelled antigen are brought into contact with an immobilized immunoadsorbent having bound thereto antibodies specific to said antigen to bind a portion of the labelled and unknown antigen thereby forming a bound fraction and an unbound fraction, and wherein the concentration of the unknown antigen is determined as a function of the bound or unbound fraction, or both, and wherein the bound fraction is released from the immunoadsorbent by rinsing the latter with an eluting medium, the improvement comprising:

flowing a mixture of a known amount of labelled antigen and an unknown and unlabelled antigen into contact with an antibody specific to said antigen wherein said antibody is covalently coupled to a water insoluble polymer which is chemically bound to a particulate substrate.

2. A radioimmunoassay procedure as set forth in claim 1 wherein said water insoluble polymer includes hydroxyl functional groups.

3. A radioimmunoassay procedure as set forth in claim 2 wherein said polymer is dextran.

4. A radioimmunoassay procedure as set forth in claim 1 wherein said substrate is a superficially porous refractory material.

5. A radioimmunoassay procedure as set forth in claim 4 wherein said polymer is bound to said material by silane linkages and wherein said antibodies are bound to said polymer by imidocarbonate linkages.

* * * * *